(12) United States Patent
Holm

(10) Patent No.: US 8,921,100 B2
(45) Date of Patent: Dec. 30, 2014

(54) USE OF THE ADENOVIRAL E2 LATE PROMOTER

(75) Inventor: Per Sonne Holm, Fürstenfeldbruck (DE)

(73) Assignee: Technische Universität München, München (DE)

( * ) Notice: Subject to any disclaimer, the term of this patent is extended or adjusted under 35 U.S.C. 154(b) by 0 days.

(21) Appl. No.: 12/498,208

(22) Filed: Jul. 6, 2009

(65) Prior Publication Data

US 2010/0015700 A1    Jan. 21, 2010

Related U.S. Application Data

(62) Division of application No. 10/492,802, filed as application No. PCT/EP02/11527 on Oct. 15, 2002, now Pat. No. 7,572,633.

(30) Foreign Application Priority Data

Oct. 16, 2001   (DE) .................................. 101 50 984

(51) Int. Cl.
| | |
|---|---|
| *C12N 15/00* | (2006.01) |
| *C12N 15/09* | (2006.01) |
| *C07H 21/04* | (2006.01) |
| *C12N 15/86* | (2006.01) |
| *A61K 48/00* | (2006.01) |
| *C12N 15/85* | (2006.01) |
| *C07K 14/47* | (2006.01) |

(52) U.S. Cl.
CPC ................ *C12N 15/86* (2013.01); *A61K 48/00* (2013.01); *C12N 15/85* (2013.01); *C12N 2710/10341* (2013.01); *C07K 14/4702* (2013.01)

USPC ...................... 435/320.1; 536/23.72; 536/24.1

(58) Field of Classification Search
CPC .... A61K 48/00; C07K 14/4702; C12N 15/86; C12N 15/85; C12N 2710/10341
USPC ............................ 435/320.1; 536/23.72, 24.1
See application file for complete search history.

(56) References Cited

U.S. PATENT DOCUMENTS 5,994,132 A * 11/1999 Chamberlain et al. ........ 435/369
7,195,896 B2 * 3/2007 Kovesdi et al. ............... 435/91.4

FOREIGN PATENT DOCUMENTS

WO       WO 97/16547      *  5/1997

OTHER PUBLICATIONS

Bhat et al., 1987, EMBO Journal, vol. 6, No. 7, p. 2045-2052.*
Wickham et al., 2003, US 20030099619 A1.*
Goding,C.R., Temperley, S.M., and Fisher, F., "Multiple transcription factors interact with the adenovirus-2 Ell-late promoter: evidence for a novel CCAAT recognition factor," Nucleic Acids Research, vol. 15, No. 19, IRL Press Limited, Oxford, England, 1987.
Huang et al., Gene Therapy, 10, 1241-1247 (2003).

* cited by examiner

*Primary Examiner* — Shin Lin Chen
(74) *Attorney, Agent, or Firm* — Michael Best & Friedrich LLP

(57) ABSTRACT

The invention relates to a nucleic acid construct comprising an adenoviral E2 late promoter or a fragment thereof and a nucleic acid. The nucleic acid is selected from the group of transgenes, genes and nucleic acids which are respectively different from adenoviral nucleic acid controlled by an E2 late promoter. The invention also relates to the uses of said nucleic acid construct.

2 Claims, 2 Drawing Sheets

SEQUENCE LISTING

```
<160> NUMBER OF SEQ ID NOS: 2

<210> SEQ ID NO 1
<211> LENGTH: 74
<212> TYPE: DNA
<213> ORGANISM: Adenovirus
<220> FEATURE:
<221> NAME/KEY: misc_feature
<223> OTHER INFORMATION: Fragment of the E2 late promoter

<400> SEQUENCE: 1
atttgtacct gaggactacc acgcccacga gattaggttc tacgaagacc aatcccgccc    60
gccaaatgcg gagc                                                     74

<210> SEQ ID NO 2
<211> LENGTH: 41
<212> TYPE: DNA
<213> ORGANISM: Adenovirus
<220> FEATURE:
<221> NAME/KEY: misc_feature
<223> OTHER INFORMATION: Fragment of the E2 late promoter

<400> SEQUENCE: 2
ccacgagatt aggttctacg aagaccaatc ccgcccgcca a                       41
```

USE OF THE ADENOVIRAL E2 LATE PROMOTER

CROSS REFERENCE TO RELATED APPLICATIONS

Figure 1:
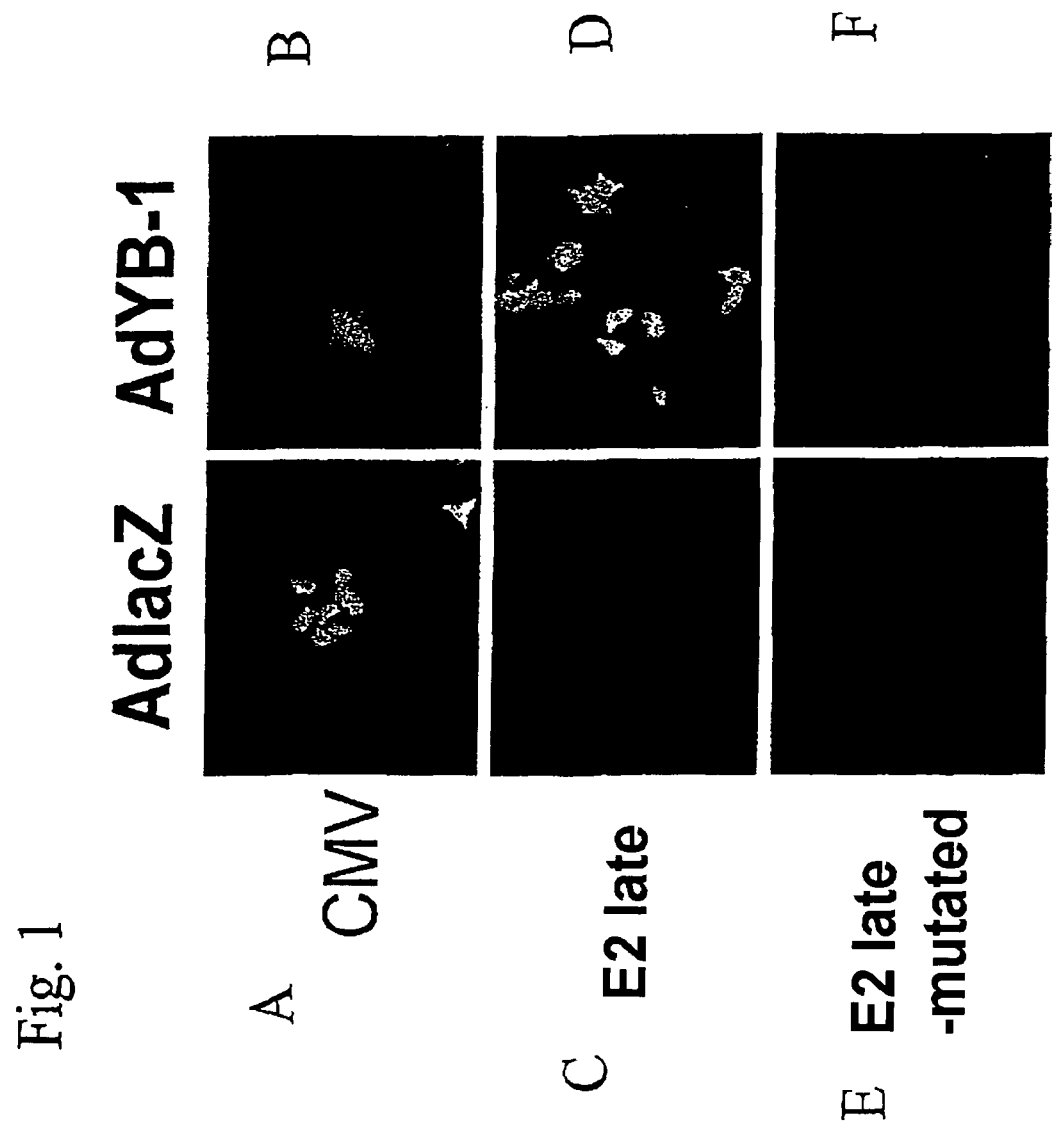

This is a divisional of U.S. application Ser. No. 10/492,802, filed Oct. 22, 2004, now U.S. Pat. No. 7,572,633, which is 371 application of International Patent Application No. PCT/EP02/11527, filed Oct. 15, 2002, which claims priority to DE 10150984.7 filed on Oct. 16, 2001, the contents each of which are fully incorporated herein by reference.

REFERENCE TO THE SEQUENCE LISTING

Reference is made to the Sequence Listing submitted herewith consisting of a file named "SL.txt" (1 KB, created Sep. 23, 2009), and the contents of which are incorporated herein by reference.

The present invention relates to the use of an adenoviral E2 late promoter, a nucleic acid construct comprising an adenoviral E2 late promoter, a vector comprising this nucleic acid construct and the use of the nucleic acid construct.

Numerous therapy concepts are being followed up at present in the treatment of tumours. Apart from using surgical techniques, chemotherapy and radiotherapy are to the fore. However, all these techniques are associated with not inconsiderable side effects for the patient.

By using replication-selective oncolytic viruses, a new technological platform has been created for the treatment of tumours. In this case, a selective intratumour replication of a viral agent is brought about which subsequently leads to virus replication, lysis of the infected tumour cells and spreading of the virus to neighbouring tumour cells. As a result of the restriction, to tumour cells, of the ability of the virus to replicate, normal tissue is spared infection and consequently lysis by the virus. Examples of such replication selective oncolytic viruses are the gene attenuated adenovirus and Herpes viruses (Martuza, R. et al. Science 252, 854-858 (1991); Fueyo, J et al. Oncogene 19, 2-12 (2000)).

Adenoviruses are well known in industry. They consist of dsDNA viruses (Boulanger, P et al. (1991); Biochem J. 275, 281-299). The complete nucleotide sequence of the adenoviral genome is known and has been described (Chroboczek, J. et al., Virology 1992, 186, 280-285). A part of the genome which is particularly important for the use of adenoviruses consists of the so-called early genes and their gene products referred to as E1, E2, E3 and E4. E1 comprises two gene products, namely E1A and E1B, which represent oncogenes. The gene products, three in total, of group E2 participate in the replication together with the gene products E3 and E4.

An example of an oncolytic adenovirus is dl 1520 (Onyx-015), which has already been successfully used in clinical phases I and II (Khuri, F. et al. Nature Medicine 6, 879-885 (2000). Onyx-015 is an adenovirus in the case of which the E1B 55 kDa gene has been deleted. The E1B 55 kDa gene product participates in the inhibition of p53, the transport of viral mRNA and the termination of protein synthesis of the host cell. In this case, the inhibition of p53 takes place by the formation of a complex from p53 and the adenovirus-encoded E1B kDa protein. P53, TP53 when encoded, effects complex regulatory mechanism (Zambetti, G. P. et al., FASEB J, 7, 855-865), which, among other things, leads to an efficient replication of viruses, such as adenoviruses, being suppressed in the cell. The gene TP53 is deleted or mutated in approximately 50% of all human tumours with the consequence that no—desirable—apoptosis occurs as a result of chemotherapy or radiotherapy and consequently the success of this tumour treatment fails to materialise in normal cases.

DNA tumour viruses such as adenoviruses propel the infected cells into the S phase of the cell cycle in order to facilitate viral DNA replication. Onyx-015 does not express the E1B 55 kDa protein and replicates selectively in tumour cells compared with normal cells. In addition, there is a further selectivity with the effect that those tumours which are p53 deficient undergo a comparatively stronger necrosis as a result of the viral lysis of the tumour cells, than those exhibiting the p53 wild type (Khuri et al, compare above). In spite of the effectiveness of Onyx-015 in virus-induced oncolysis in the case of tumours deficient in p53 on principle, the success rate of 15% of the treated tumours is very low. Ries et al. (Ries, D. J. et al. Nature Medicine 6, 1128-1132 (2000)) have shown a basic possibility of how to successfully use Onyx-015 also for tumours with p53 wild type. In this case, the tumour suppressor protein p14ARF is not expressed. As a result of the absence of p14ARF, the normal reaction of the p53 system vis-à-vis a viral infection does not occur thus allowing the replication of Onyx-015 also in these tumours. However, the practical application of this knowledge presupposes that a suitable genetic background exists in the tumour cell or is provided by suitable therapeutic measures. In the former case, the number of tumours treatable by Onyx-015 would be further reduced, in the second case, a time consuming/complicated modification of the genetic background of the tumour cells would be required.

In one aspect, the problem underlying the present invention is to provide a promoter which allows a tumour-specific expression of nucleic acids. In another aspect, the invention is based on the objective of providing a medicament for the therapy of YB-1 positive diseases, in particular of tumour diseases.

According to the invention, the objective is achieved in a first aspect by the use of an adenoviral E2 late promoter or a fragment thereof for the expression of genes which are different from the adenoviral genes or adenoviral nucleic acids controlled by the E2 late promoter in a naturally occurring adenovirus.

In a second aspect, the task according to the invention is achieved by the use of an adenoviral E2 late promoter or a fragment thereof for the expression of a transgene or a transgenic nucleic acid.

In one embodiment of the uses according to the invention, it is provided for the promoter fragment to comprise a sequence according to SEQ. ID. No. 1.

In an alternative embodiment of the uses according to the invention it is provided for the promoter fragment to exhibit a sequence according to SEQ. ID. No. 2.

In one embodiment of the uses according to the invention, it is provided for the promoter and/or the promoter fragment to exhibit a binding site for YB-1.

In a further embodiment of the uses according to the invention it is provided for the promoter and/or the fragment to exhibit at least one element selected from the group comprising the Y-box, the TATA box and the SPI binding site.

In an even further embodiment of the uses according to the invention it is provided for the promoter and/or the promoter fragment to exhibit YB-1 in the bound form.

In one embodiment of the uses according to the invention it is provided for the transgene and/or the adenoviral gene controlled by the E2 late promoter and/or the nucleic acid controlled by the E2 late promoter to be selected from the group of genes comprising apoptosis-inducing genes, genes for prodrug systems and genes for protease inhibitors.

In one embodiment of the uses according to the invention it is provided for the transgene or the adenoviral genes or nucleic acid(s) controlled by the adenoviral E2 late promoter to be selected from the group comprising antisense molecules, ribozymes and aptamers.

In a third aspect, the objective of the invention is achieved by a nucleic acid construct comprising an adenoviral E2 late promoter or a fragment thereof and a nucleic acid, the nucleic acid being selected from the group comprising transgenes, genes and nucleic acids which are respectively different from the adenoviral nucleic acids controlled by an E2 late promoter.

In one embodiment it is provided for the promoter fragment to comprise a nucleic acid sequence selected from the group comprising SEQ. ID. No. 1 and SEQ. ID. No. 2.

In a fourth aspect, the objective according to the invention is achieved by a vector comprising a nucleic acid construct according to the invention.

In a fifth aspect, the objective according to the invention is achieved by the use of a nucleic acid construct according to the invention for the preparation of a medicament.

In one embodiment it is provided for the medicament to be used for the treatment of tumours.

In a further embodiment it is provided for the tumours to be those exhibiting YB-1 in the nucleus.

In an even further embodiment it is provided for the tumours to be those exhibiting YB-1 in the nucleus, preferably exhibiting YB-1 in the nucleus in the presence of a stress factor.

In one embodiment it is provided for the stress factor to be selected from the group comprising hypothermia, UV exposure and exposure vis-à-vis cytostatics.

In an even further embodiment it is provided for the medicament to be used together with cytostatics and/or hypothermia.

Finally, in an even further embodiment it is provided for the tumour to exhibit tumour cells with multi-drug resistances.

The present invention is based on the surprising finding that YB-1 in the nucleus binds to the adenoviral E2 late promoter and this promoter is highly suitable for the expression of nucleic acids which are different from those nucleic acids which are controlled in an adenoviral system, i.e. in a naturally occurring adenovirus, by the E2 late promoter. Moreover, it has surprisingly enough been found that the adenoviral E2 late promoter, on the one hand, is a very strong promoter and, compared with the CMV promoter used as gold standard, is only negligibly weaker in the presence of a practically non-existent background expression in the case that the promoter is not active.

The use, according to the invention, of the adenoviral E2 late promoter is determined in particular by its regulatibility by YB-1, YB-1 being effective as a positive effecter, i.e. the promoter is active only in the presence of YB-1 in the nucleus. In this respect, said adenoviral E2 late promoter can be regulated in a highly selective manner and is consequently usable in systems in which YB-1 is present in the nucleus and practically any expression of the nucleic acid being subject to the control of the adenoviral E2 late promoter is prevented in the case where YB-1 is not present in the nucleus as effecter or regulator.

YB-1 is a representative of the Y box protein family which binds to the DNA sequence motive Y-box. The Y-box motive represents a transcriptionally regulatory element which is present in the promoter regions or enhancer regions of a number of different genes which play a part in the regulation of cell proliferation (Ladomery, M. et al. 1995; Bioassays 17: 9-11 Didier, D. K. et al, 1988, PNAS, 85, 7322-7326).

The details provided here apply also to fragments of the said adenoviral E2 late promoter which, herein, will also occasionally be referred to as E2 late promoter or later on as E2 promoter, and in particular to those promoter fragments disclosed herein and referred to as SEQ. ID. No. 1 and SEQ. ID. No. 2.

The nucleic acid sequence according to SEQ. ID. No. 1 is as follows:

5' atttgtacctgaggactaccacgcccacgagattaggtt ctacgaagaccaatcccgcccgccaaatgcggagc- 3'

The Y box (CAAT) considered relevant for the binding of YB-1 is printed in bold.

The sequence according to SEQ. ID. No. 1 is the range of positions −22 to −96 of the E2 late promoter.

The nucleic acid sequence according the SEQ. ID. No. 2 is as follows:

5' ccacgagattaggttctacgaagaccaatcccgcccgccaa- 3'

The nucleic acid sequence according to SEQ. ID. No. 2 comprises the range of positions −47 to −87 of the E2 late promoter.

In addition, it is within the scope of the present invention that each fragment or derivative of the promoter can be used for as long as it is capable of binding YB-1 and still exhibits a promoter activity. Without wishing to be restricted thereto, binding of YB-1 appears to take place to the Y box or the Y box seems to participate in the formation of secondary structures as a result of which the presence of this box is significant for the formation of the adenoviral E2 late promoter and corresponding fragments used according to the invention.

The E2 late promoter of adenovirus has been described, for example, by Swaminathan, S., and Thimmapaya, B. (1995) Curr. Top. Microbiol. Immunol., 199, 177-194. In the adenoviral system, the E2 late promoter, together with the E2 early promoter, has the function of controlling the adenoviral E2 region and/or genes E2A and E2B. In this case, the synthesis of the E2 mRNA takes places initially starting out from the E2 early promoter. Approximately five to seven hours after the infection of a cell, a switch-over to the E2 later promoter takes place. The mechanism on which this process is based is not yet known at present.

In the early phase of infection with adenoviruses, two mRNA products of the E1A region are first produced, which products are 13S or 12S in size. Investigations have shown that the E1A 12S protein prevents and/or represses the activation of the E2 region via the E2 late promoter. The gene encoding for the E1A 13S protein, on the other hand, activates the E2 region and/or genes via the E2 early promoter (Guilfoyle R A, Osheroff W P, Rossini, EMBO J 1985, 4, 707-713).

Moreover, it is known that a deletion of the region of the range of the nucleotides −51 to −33 of the E2 late promoter represses the synthesis of the E2 region almost completely (Guilfoyle R A et al, compare above).

It is within the scope of the present invention that it is possible for any adenoviral E2 late promoter to be used. Such different adenoviral E2 late promoters can be determined by the different forms of the adenoviruses such as they are known in the state of the art. At present, approximately 50 sub-types are known in the state of the art each of which could, in principle, be used within the scope of the present invention either as a vector or as source of an E2 late promoter.

The E2 late promoter exhibits a number of structural and sequential characteristics which may be significant for its use and in particular the use of fragments of the promoter. The formation of a loop in the range of the nucleotides of −47 to −81 is such a characteristic, position −1 denoting directly the first nucleotide which is transcribed under the control of the promoter. This loop is an integral part of the two fragments, disclosed herein, of the E2 late promoter which also exhibit the properties described herein for the complete E2 late promoter. A second feature which is preferably contained in the functionally active fragments of the E2 late promoter is the so-called Y-box which appears to be responsible for binding of the YB-1 protein. Further elements which may form part of preferred embodiments of the E2 late promoter and the fragments according to the invention are the TATA box and SPI binding site. In this respect, the TATA box is important for the initiation of transcription and is usually situated at a distance of approximately 25 to 32 bp upstream of the transcription initiation site. A further feature of the E2 late promoter and/or of a functionally active fragment thereof, which may optionally be present either individually or as a complement to the other features described above, is the so-called SPI binding site. The SPI binding site is formed by the so-call GC box which binds to the transcription factor SPI. More than one GC box may be present per promoter.

The nucleic acid construct disclosed herein and/or the E2 late promoter or a functionally active fragment thereof can be present either in a form in which YB-1 is bound or in a YB-1-free form. If YB-1 is bound, the promoter is functionally active and a transcription may occur in a suitable transcription system; in the absence of YB-1, the promoter is not active so that no transcription can be observed in a transcription system. Suitable transcription systems have been described, for example, by Lewin, B., Gene: Lehrbuch der molekularen Genetik VCH Verlagsgesellschaft, 6490 Weinheim, Germany.

According to the present invention, it is possible for practically any nucleic acid to be subjected to the control of the adenoviral E2 late promoter which then controls the expression of the nucleic acid. In this case, the E2 late promoter is subject to the stringent control of YB-1. Both genes and generally encoding sequences or fragments thereof can in this case be used as possible nucleic acids, but also non-encoding nucleic acids. In the case of the expression of nucleic acids encoding in the widest sense and their control by the E2 late promoter, it is anticipated that the requirements generally applying to promoters are satisfied, i.e. a suitable initiation codon exists and the promoter is positioned at a distance from the initiation codon such that a translation is possible. The same applies, in principle, also regarding the requirements existing for transcription.

In principle, it is within the scope of the present invention that any encoding nucleic acid can be used. With a view to the specific regulatibility of the promoter by YB-1 and consequently the use of the vector in a biological system characterised by the absence or presence of this effecter, preferred combinations of encoding sequences with the E2 late promoter are obtained. Since YB-1 is associated in particular with different tumour events, preferred nucleic acids may consist of those which may be important in the treatment of tumours at the molecular level. These include apoptosis inducing genes, for example. By introducing such genes into tumours cells exhibiting YB-1 in the nucleus (for example 30% of the ovarian carcinoma [Kamura et al., 1999; Cancer, 85, 2450-2454, Shibao K, Takano H, Nakayama Y, Okazaki K, Nagata N, Izumi H, Uchiumi T, Kuwano M, Kohno K, Itoh H Enhanced coexpression of YB-1 and DNA topoisomerase II alpha genes in human colorectal carcinomas. Int J Cancer 1999 Dec. 10; 83(6):732-7]), be it natural or induced, it is only the tumour cells which are capable of expressing the genes coupled to the promoter with the result that apoptosis caused by the apoptosis inducing gene takes place only in these cells. The situation is similar for other genes introduced in this way. Preferably, those genes are introduced which lead to a modification of the behaviour of the cells such as the tumour character of the cells and/or to selective killing of the tumour cells, for example. Apart from apoptosis genes, those genes can be introduced which interfere with the cellular events in a highly indirect manner, such as protease inhibitors, for example. Such protease inhibitors should, in general, inhibit the invasive behaviour and/or metastasis of the tumours. These include matrix metallo proteases (MMP), plasminogen activator systems (uPA), cathepsin. Moreover, the E2 late promoter can be used, according to the invention, for controlling the expression of viral proteins, viral proteins being those which normally, i.e. in the naturally occurring adenoviruses, are not subject to the control of E2 late promoter. In particular, they are the viral proteins E3ADP, E4orf6 and E1B55k. E4orf6 is a multifunctional protein which is required for maximum viral DNA replication and particle formation. It also plays an important part in splicing and the transportation of the viral RNA. In addition, it interacts with the viral protein E1B55k in order to accelerate the inactivation of p53. E1B55K, too, is a multifunctional protein which promotes, in interaction with the E4orf6 protein, the export of the viral RNA, whereas the cell-inherent RNAs are retained in the cell nucleus. A further important function of E1B55k consists of inactivating, either alone and/or together with E4orf6, the cellular protein p53. E3ADP, also referred to as adenoviral death protein, is an integral membrane glycoprotein which is required for an efficient cell lysis and the liberation of the newly synthesised viruses. The viral proteins mentioned above are known to the experts in this field and have been described in the literature.

The selective killing of the cells can take place either directly as a result of the influence of the genes introduced or indirectly as a result of the changes in the cells caused by the introduced genes. Such a change can, for example, lead to further compounds supplied from outside acting on the cells first and consequently leading to a killing of the tumour cells, for example. An example of this approach is provided by genes which need to be ascribed to the prodrug system. The prodrug system is a system in particular of enzymes which lead to metabolically non-active chemical compounds supplied to an organism as a medicine, for example, being converted into the pharmaceutically effective form only in the body. The thymidine kinase system (TK system), for example, is an example of a prodrug. It is based on the expression of the Herplex simplex thymidine kinase gene (HSVtk) following the addition of the prodrug ganciclovir. This is non-toxic to man in this form. Thymidine kinase phosphorylates the ganciclovir substrate. A purin analogue is formed which is toxic. A further example is provided by the cytosin desaminase gene system (CD).

Coupling of the adenoviral E2 late promoter to a non-encoding nucleic acid is possible also to an rRNA or tRNA, for example. In this respect, an enhanced expression of this RNA population which is essential for the functioning of a cellular system is possible, which populations may in turn be associated with numerous cellular effects and functions.

A further form of the non-encoding nucleic acids which may be subjected to the control of the adenoviral E2 late promoter are aptamers, ribozymes, antisense molecules and siRNA. Aptamers are nucleic acids, preferably ribonucleic acids which bind specifically to a target molecule vis-à-vis which they have been selected. The preparation of such aptamers has been described in European patent EP 0 533 838, for example. A further group of nucleic acids which can be subjected to the control of the adenoviral E2 late promoter consists of the antisense molecules whose principle of action is based on the fact that these molecules form a complex with mRNA and thus prevent the translation of the mRNA. In one embodiment, antisense molecules are also known in such a form that the cellular RNase H system is activated and, as a result of the enzymatic activity of the RNase H system, the mRNA complexed or hybridised with the antisense molecule is degraded.

Finally, the non-encoding nucleic acid can also consist of ribozymes, i.e. nucleic acids which are catalytically active and capable of splitting, i.e. hydrolysing, either intramolecular or intermolecular nucleic acids, in particular ribonucleic acid. As a result of the sequence specificity of ribozymes, it is possible to selectively hydrolyse specific nucleic acid populations in a biological system, such as a cell, thus influencing biological processes.

The nucleic acid construct disclosed herein can be designed to the extent such as it has been described above for the different uses of the E2 late promoter and fragments thereof.

The nucleic acid construct can be present in different forms. It is thus within the scope of the present invention for the nucleic acid construct to be part of a vector. Such vectors are known to the persons skilled in the art and comprise plasmids and viruses, for example. Preferably, the vectors are those for eukaryotic cells, in particular for mammalian cells. Viral vectors comprise, among others, adenoviral vectors, retroviral vectors, adeno-associated vectors (AAV) and Herpes simplex vectors. All vectors have been mentioned and/or described by Dougherty, G J, Chaplin, D., Dougherty, S T., Chiu, R K, McBridge, Wh. In vivo gene therapy of cancer, Tumour Targeting, 2, 106-114 (1996); Advances in Pharmacology: Gene Therapy, Editor J. Thomas August, Volume 40, Academic Press.

The nucleic acid construct according to the invention can be used in general for the preparation of medicaments. In this respect, there are no restrictions regarding the type of indication for such medicaments for as long as the medicaments are characterised in that they are formed and/or become effective by using the adenoviral E2 late promoter or a functionally active fragment thereof as disclosed herein. In other words, medicaments according to the meaning of the present invention include those which consist of known genes or general nucleic acids provided these are subject to the control of the adenoviral late E2 promoter or a functionally active fragment thereof.

A preferred indication regarding the use of the medicaments according to the invention is represented by tumour diseases. This is due to the binding of YB-1, disclosed herein, to the adenoviral E2 late promoter and the specific regulatibility of the promoter, which is based thereon, such that each nucleic acid which is subject to the control of the adenoviral E2 late promoter or a functionally active fragment thereof is specifically expressed in tumour cells exhibiting YB-1 in the nucleus. Normal, in particular human, cells possess YB-1 only in the cytoplasma such that these do not exhibit any expression of the nucleic acid which is subject to the control of the adenoviral E2 late promoter or a functionally active fragment thereof.

As a result of the coupling of the activation of the nucleic acid which is subject to the control of the adenoviral E2 late promoter or a functionally active fragment thereof with YB-1 present in the cell nucleus, it is possible to treat with the nucleic acid construct according to the invention also those diseases and in particular tumour diseases in the case of which YB-1 is present in the cell nucleus only if certain conditions exist which lead to the YB-1 being present in the nucleus exclusively, mainly or to an extent increased vis-à-vis the absence of the said specific conditions. Within the region of the tumour diseases, the localisation of YB-1 in the nucleus can be effected by the cells being exposed to stress factors. Such stress factors include, for example, hypothermia, UV radiation or the treatment of the cells or the organism containing these by cytostatics. Such cytostatics comprise cisplatinum, among others.

Further cells which are basically accessible to the treatment by the nucleic acid construct according to the invention are the so-called multi-drug resistant tumour cells. Multidrug resistance is caused by the synthesis of P-glycoprotein. The connection between YB-1 and MDR-1 gene expression (MDR multiple drug resistance) has been described by Bagou et al. (Bagou, R. C. et al., Nature Med. 3, 1997, 4: 447-450). As a result of this connection, those tumour cells and tumours containing them which are P-glycoprotein positive can be addressed and treated by the nucleic acid construct according to the invention.

Figure 2:
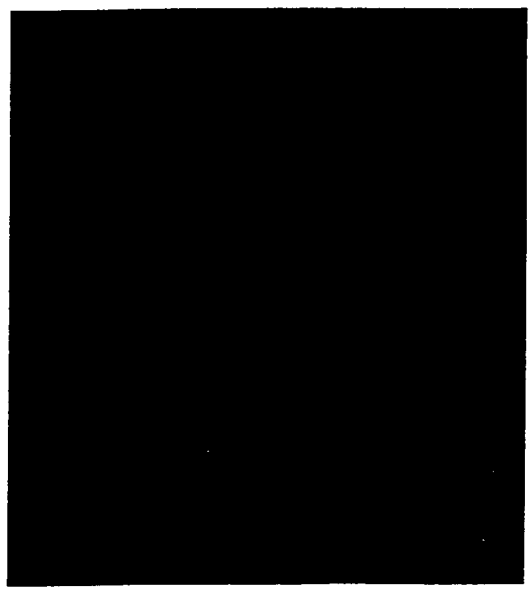
Figure 2:
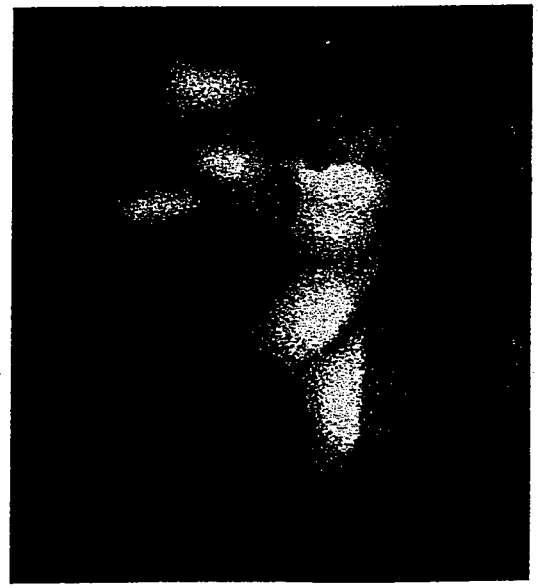

The invention will be illustrated in the following by the figures, examples and sequence listing from which further features, embodiments and advantages of the invention can be derived. In these FIG. 1 shows fluorescence microscopic images of U2OS cells which have been transfected with a vector encoding green fluorescent protein subject to the control of the CMV promoter (FIGS. 1A, 1B), the control of the E2 late promoter (FIGS. 1C, 1D) and the control of an E2 late promoter mutating in the YB-1 box (FIGS. 1E, 1F) following the infection with an E1/E3 deleted adenovirus (FIGS. 1A, 1C, 1E) and a YB-1 expressing E1/E3-deleting adenovirus (FIGS. 1B, 1D. 1F) and FIG. 2 shows fluorescence microscopic images of YB-1 nucleus-negative U2OS cells (FIG. 2A) and YB-1-nucleus-positive cells (FIG. 2B) following transfection with a plasmid encoding green fluorescent protein subject to the control of the adenoviral E2 late promoter.

EXAMPLES

Example 1

The E2 Late Promoter is YB-1 Specific

The E2 late promoter was cloned in the vector pGL3 enhancer (Promega) into the XhoI and HindIII interface. This vector possesses the luciferase gene or, alternatively, the GFP gene as reporter gene. As soon as GFP is expressed, the cells light up green. Firstly, 200,000 U2OS cells per well were presented in the plate of 6 such wells. After 24 hours, the transfection of the different vectors containing the different fragments of the E2 late promoter was effected by Superfect in line with the manufacture's instructions (Qiagen). The plasmids were produced from the pGL3 enhancer vector, Promega, the luciferase gene being replaced by the reporter gene GFP (green fluorescent protein).

After a further 24 hours, the cells were infected with 50 pfu/cell using a E1/E3-deleted adenovirus (AdlacZ, left hand column of FIG. 1) and AdYB-1 (right hand column of FIG. 1). AdYB-1 is an E1/E3 deleted adenovirus which expresses the transcription factor YB-1 as a transgene. After a further 24 hours, the evaluation took place under a fluorescence microscope. The result clearly shows that only the intact E2 late promoter is activated by the expression of YB-1 as illustrated in FIG. 1D. The cells illustrated in FIGS. 1A and 1B were transfected as positive controls using plasmid constructs in the case of which the green fluorescent protein was subjected to the control of the cytomegalovirus promoter (CMV). In the case of the constructs or tests illustrated in FIGS. 1C and 1D, the E2 late promoter was used according to the invention, i.e. the expression of the green fluorescent protein was subjected to the control of this promoter. In the case of the cells illustrated in FIGS. 1E and 1F, a mutated E2 late promoter of adenovirus was used instead of the E2 late promoter of adenovirus. The mutation was situated in the YB-1 box, the sequence GCCTG instead of ATTGG being used.

Example 2

The E2 Late Promoter is Specific for YB-1 Nucleus-Positive Cells

For the investigation of the specificity of the E2 late promoter in resistant YB-1 nucleus-positive cells, the following experiment was carried out.

2,000,000 cells per well were presented in a plate of 6 wells. A synthesised E2 late promoter in pGL3 enhancer vector (obtainable from Promega) with the reporter gene GFP was transfected by Superfect from Qiagen in line with the manufacturer's instructions 24 hours later into the cells. After a further 48 hours, the evaluation took place under a fluorescence microscope.

FIG. 2A shows the result of the osteosarcoma cells U2OS which exhibit no YB-1 in the nucleus. In FIG. 2B, the result is illustrated using multi-drug resistant stomach carcinoma cells 257RDB. In the case of these cells, YB-1 is localised in the cell nucleus. The result clearly shows that the reporter gene GFP is activated via the E2 late promoter only in YB-1 nucleus-positive 257RDB cells.

The characteristic features of the invention disclosed in the above description, the claims and the drawings can be essential either individually or in any desired combination for effecting the invention in its various embodiments.

The invention claimed is:

1. An adenoviral vector suitable for use in the treatment of a tumor disease, wherein the tumor cells express YB-1 and have YB-1 in the nucleus, wherein the adenoviral vector comprises an adenoviral E2 late promoter or a fragment thereof and a nucleic acid under the control of the adenoviral E2 late promoter or the fragment thereof, wherein the nucleic acid being selected from the group consisting of adenoviral gene E1B, adenoviral gene E4orf6, and combination thereof; and wherein the adenoviral E2 late promoter or fragment thereof is regulated by YB-1.

2. The replication-selective oncolytic adenoviral vector of claim 1, wherein the adenoviral E2 late promoter fragment comprises a nucleic acid sequence selected from the group consisting of SEQ ID NO:1 and SEQ ID NO:2.

* * * * *